(12) United States Patent
Pettine

(10) Patent No.: US 9,980,984 B2
(45) Date of Patent: May 29, 2018

(54) TREATMENT OF INFLAMMATION OF OSTEOARTHRITIC KNEES WITH MESENCHYMAL STEM CELLS

(71) Applicant: Kenneth Allen Pettine, Ft. Collins, CO (US)

(72) Inventor: Kenneth Allen Pettine, Ft. Collins, CO (US)

(*) Notice: Subject to any disclaimer, the term of this patent is extended or adjusted under 35 U.S.C. 154(b) by 111 days.

(21) Appl. No.: 15/292,327

(22) Filed: Oct. 13, 2016

(65) Prior Publication Data

US 2018/0104280 A1    Apr. 19, 2018

(51) Int. Cl.
*A61K 35/28* (2015.01)
*A61K 9/00* (2006.01)
*A61K 35/12* (2015.01)

(52) U.S. Cl.
CPC ............ *A61K 35/28* (2013.01); *A61K 9/0019* (2013.01); *A61K 2035/124* (2013.01)

(58) Field of Classification Search
None
See application file for complete search history.

(56) References Cited

U.S. PATENT DOCUMENTS

| 8,377,432 B2 | 2/2013 | Saw |
| 9,408,874 B2 | 8/2016 | Pettine |
| 2006/0177387 A1 | 8/2006 | Slavin et al. |
| 2008/0138414 A1 | 6/2008 | Huckle et al. |
| 2012/0087983 A1 | 4/2012 | Katz et al. |
| 2012/0148548 A1* | 6/2012 | Barry .................. C12N 5/0663 424/93.7 |

FOREIGN PATENT DOCUMENTS

| WO | 200180865 A2 | 11/2001 |
| WO | 2004037130 A1 | 5/2004 |
| WO | 2012079132 A1 | 6/2012 |
| WO | 2013166156 A2 | 11/2013 |
| WO | 2014093581 A1 | 6/2014 |
| WO | 2016073989 A2 | 5/2016 |

OTHER PUBLICATIONS

Chahla (Concentrated Bone Marrow Aspirate for the Treatment of Chondral Injuries and Osteoarthritis of the Knee, 2016). (Year: 2016).*
Uth, Kristin. Stem cell application for osteoarthritis in the knee joint: A minireview World J. Stem Cells Nov. 26, 2014; 6(5): 629-636 (Year: 2014).*

(Continued)

*Primary Examiner* — Scott Long
*Assistant Examiner* — Nghi V Nguyen
(74) *Attorney, Agent, or Firm* — Bassam S. Nader; Brannon Sowers & Cracraft PC

(57) ABSTRACT

The present disclosure provides an inventive method of treating inflammation that is associated with osteoarthritis of the knee joint by injecting mesenchymal stem cells into the symptomatic knee. In one aspect, the mesenchymal stem cells are obtained autogenously. In another aspect, the mesenchymal stem cells are injected below the degenerated medial tibial plateau of the knee joint, resulting in reduction of the inflammation and alleviation of the symptoms of the osteoarthritis.

44 Claims, 4 Drawing Sheets

(56) References Cited

OTHER PUBLICATIONS

Qi, Yiying. Mesenchymal stem cell-based treatment for cartilage defects in osteoarthritis Mol Biol Rep (2012) 39:5683-5689, (Year: 2012).*
Jo, Chris. Intra-Articular Injection of Mesenchymal Stem Cells for the Treatment of Osteoarthritis of the Knee: A Proof-of-Concept Clinical Trial. Stem Cells 2014;32:1254-1266. (Year: 2014).*
Altman, R.D. et al., Atlas of Individual Radiographic Features in Osteoarthritis, Revised, 2007, pp. A1-A56, Elsevier Ltd.
Berenbaum, F., Osteoarthritis as an Inflammatory Disease (Osteoarthritis is not osteoarthrosis!), Research Society International, 2012, pp. 16-21, Elsevier Ltd.
Binkley, Jill M. et al., The Lower Extremity Functional Scale (LEFS): Scale Development, Measurement Properties, and Clinical Application, Apr. 1999, pp. 371-383, vol. 79, No. 4, Physical Therapy.
http://www.wisegeek.org/what-is-bone-inflammation.htm.
Bornes, Troy D, et al., Mesenchymal Stem Cells in the Treatment of Traumatic Articular Cartilage Defects: A Comprehensive Review, 2014, pp. 1-19, Arthritis Research & Therapy.
Centeno, Christopher J, et al., Increased Knee Cartilage Volume in Degenerative Joint Disease Using Percutaneously Implanted, Autologous Mesenchymal Stem Cells, 2008, pp. 343-353, www.painphysicianjournal.com.
Counsel, Peter D., et al., Cell Therapy in Joint Disorders, 2014, pp. 27-37, vol. 7, No. 1, Sage Publishing.
Freitag, Julien, et al., Adipose Derived Mesenchymal Stem Cell Therapy in the Treatment of Isolated Knee Chondral Lesions: Design of a Randomised Controlled Pilot Study Comparing Arthroscopic Microfracture Combined With Postoperative Mesenchymal Stem Cell Injections, 2015, pp. 1-9, BMJ Open.
Hernigou, P. et al., The Use of Percutaneous Autologous Bone Marrow Transplantation in Nonunion and Avascular Necrosis of Bone, 2005, pp. 896-902, The Journal of Bone and Joint Surgery.
Kellgren, J.H. et al., Radiological Assessment of Osteo-Arthrosis, 1957, pp. 494-502, group.bmj.com.
Kristjánsson, B. et al., Current Trends of Stem Cell-based Approaches for Knee Osteoarthritis, Jun. 1, 2013, pp. 1-6, OA Tissue Engineering.
Murphy, Matthew B., et al., Mesenchymal Stem Cells: Environmentally Responsive Therapeutics for Regenerative Medicine, 2013, pp. 1-16, Experimental & Molecular Medicine.
Merchán EC, R., Intra-Articular Injections of Mesenchymal Stem Cells for Knee Osteoarthritis, Dec. 2014, pp. 1-6, The American Journal of Orthopedics.
Sato, M. et al., Direct Transplantation of Mesenchymal Stem Cells into the Knee Joints of Hartley Strain Guinea Pigs with Spontaneous Osteoarthritis, 2012, pp. 1-10, Arthritis Research & Therapy.
Vilar, Jose M. et al., Controlled, Blinded Force Platform Analyis of the Effect of Intraarticular Injection of Autologous Adipose-Derived Mesenchymal Stem Cells Associated to PRGF-Endoret in Osteoarthritic Dogs, 2013, pp. 2-6, BMC Veterinary Research.
Xie, Xuetao, et al., Comparative Evaluation of MSCs from Bone Marrow and Adipose Tissue Seeded in PRP-derived Scaffold for Cartilage Regeneration, Biomaterials, 2012, pp. 7008-7018, vol. 33, Issue 29, Elsevier Ltd.

* cited by examiner

TREATMENT OF INFLAMMATION OF OSTEOARTHRITIC KNEES WITH MESENCHYMAL STEM CELLS

FIELD OF THE INVENTION

The present disclosure relates to an inventive method of treating inflammation associated with osteoarthritis of the knee joint by injecting mesenchymal stem cells into the symptomatic knee.

BACKGROUND OF THE INVENTION

It is estimated that osteoarthritis ("OA") affects about 50 million Americans. Osteoarthritis is a process that can occur in any joint where the articular cartilage diminishes in thickness as one ages. This process continues throughout one's life until all the articular cartilage is gone. Thereafter, in the case of osteoarthritic knee joints, weight applied on the knee results in bone on bone wear. In most cases this process is associated with gradual, increasing pain, to the point that any walking can be unbearable. Osteoarthritis of the knee may also be associated with night pain that can severely inhibit a normal sleep pattern.

Osteoarthritis of the knee is an almost ubiquitous condition in humans over the age of 60. Osteoarthritis of the knee does typically affect the medial tibiofemoral joint. Many people develop gradual degradation of the articular cartilage on the medial aspect of their knee, which results in their knees becoming progressively bowlegged or genu varum. Often the pain of the arthritis is felt along the medial side of the knee and specifically the proximal tibial plateau. MRI scanning often shows a hyperemic area just beneath the medial part of the knee joint in the metaphysis of the tibia. The knee joint consists of the medial and lateral femoral tibial compartments and the patella-femoral joint. Osteoarthritis can primarily impact any one of these areas or all three. It is known that the most common type is osteoarthritis of the medial tibial femoral joint.

The American Academy of Orthopedic Surgeons ("AAOS") recommended treatments for osteoarthritis of the knee include the following: weight loss, gentle exercise, anti-inflammatory medications followed by total knee replacement. The AAOS does not recommend arthroscopic debridement or any hyaluronic acid products such as SYN-VISC®, EUFLEXXA™, ORTHOVISC®, SUPARTZ™, or HYALGAN® for treating knee osteoarthritis. In the past, hundreds of thousands of knee arthroscopies were performed to lavage the knee with saline and debride frayed articular cartilage. This treatment has been shown in prospective randomized studies to have no efficacy and in fact often accelerates the degeneration of the articular cartilage. Four prospective randomized studies have shown no benefit over placebo at six-month follow-up with these hyaluronic acid injections. Despite the fact hyaluronic acid products have shown no efficacy, the market for these products is several hundred million dollars per year. One substantial reason for this may be the huge void between non-operative treatments and the only surgical treatment, total knee arthroplasty.

Last year in the United States over 900,000 total hip and knee replacements were performed with a direct cost of over $30 billion. These numbers are expected to double in the next three years. Additionally, it has been reported that every day 10,000 people in the United States turn 65 years of age, and that this will continue for the next 14 years.

OA has long been considered a "wear and tear" disease leading to loss of cartilage. OA used to be considered the sole consequence of any process leading to increased pressure on one particular joint or fragility of cartilage matrix. Progress in molecular biology in recent decades has profoundly modified this paradigm in favor of an "inflammatory" paradigm. Recent reports have shown that subchondral bone may have a substantial role in the OA process, as a mechanical damper, as well as a source of inflammatory mediators implicated in the OA pain process and in the degradation of the deep layer of cartilage. Thus, initially considered cartilage driven, OA is now considered to be a much more complex disease with inflammatory mediators released by cartilage, bone and synovium. Low-grade inflammation induced by the metabolic syndrome, innate immunity and inflammaging are some of the more recent arguments in favor of the inflammatory paradigm of OA. (See, Berenbaum, F., "*Osteoarthritis as an inflammatory disease (osteoarthritis is not osteoarthrosis!),*" *Osteoarthritis and Cartilage,* 21:16-21 (2013)). (See also: Sokolove, J. et al., "*Role of inflammation in the pathogenesis of osteoarthritis: latest findings and interpretations,*" *Ther Adv Musculoskel Dis,* 5(2):77-94 (2013)).

Bone inflammation, also known as osteitis, is a condition that causes bone to become thickened or swollen. This increase in mass may result in bone distortion, such as bowing or arching of a straight long bone. When the bone begins to change shape, it can also produce pain by altering weight bearing positions or increasing pressure against other internal structures of the body.

To understand osteitis, it is important to understand the roles of inflammation and pain in the healing process. Inflammation is the body's natural response to fight off anything that compromises homeostasis, or internal balance. Swelling protects an area and calls on more blood to travel there to initiate the healing process. The accompanying pain symptoms are the body's warning system. Pain is also a protective mechanism to hinder excessive movements which may cause further injury.

When bone sustains an injury that disrupts normal function, such as a fracture, it increases the risk of infection. The body, in turn, may cause inflammation to help rid itself of invading contaminants. Osteomyelitis, for example, is a bone infection that causes inflammation. This infection travels through the blood to the inside of the bone and affects the marrow. The marrow, which consists of vascular tissue, is located in the middle of the bone and is responsible for creating new blood cells.

Periostitis occurs when the protective bone covering or periosteum is involved in the inflammatory process. This condition can occur with an infection process, or it may be triggered by excessive external pressure created by the surrounding muscles.

When there is damage to the joints that connect bones, as with arthritis conditions, bone inflammation and pain issues can occur. The arthritis common as part of the aging process is called osteoarthritis and affects the entire bone. It can cause destruction of the bone or produce abnormal ridges or projections. Osteoarthritis may also be activated by certain diseases.

Bones constantly regenerate by a process called bone remodeling. Paget's disease, which may also lead to osteoarthritis, is a health condition that disturbs normal bone remodeling. This can cause bones to form irregularly resulting in deformity, a loss of overall bone strength and inflammation.

Successful treatment of inflammation depends on treating the cause. If it is produced by an infection, symptoms will continue until the infection is eliminated. With health conditions that cause permanent damage to the joints or bones, a comprehensive exercise and strengthening program may help alleviate painful symptoms and may also aid in the restoration of range of motion. In severe cases, surgical correction of the bone may be necessary.

Mesenchymal stem cells (MSCs), after their initial discovery in bone marrow, have been isolated and characterized from several adult and fetal tissues, including adipose (fat), dermis (skin), synovial fluid, periosteum, umbilical cord blood, placenta and amniotic fluid. MSCs are partially defined by their ability to differentiate into tissues including osteoblasts (bone cells), chondrocytes (cartilage cells), myocytes (muscle cells), and adipocytes (fat cells). But it is believed that it is their trophic, paracrine and immunomodulatory functions that may have the greatest therapeutic impact in vivo. Unlike pharmaceutical treatments that deliver a single agent at a specific dose, MSCs are site regulated and secrete bioactive factors and signals at variable concentrations in response to local microenvironmental cues. Significant progress has been made in understanding the biochemical and metabolic mechanisms and feedback associated with MSC response. The anti-inflammatory and immunomodulatory capacity of MSC may be paramount in the restoration of localized or systemic conditions for normal healing and tissue regeneration. Allogeneic MSC treatments, categorized as a drug by regulatory agencies, have been widely pursued, but new studies demonstrate the efficacy of autologous MSC therapies, even for individuals affected by a disease state. Safety and regulatory concerns surrounding allogeneic cell preparations make autologous and minimally manipulated cell therapies an attractive option for many regenerative, anti-inflammatory and autoimmune applications. (See, Murphy, M. B., et al., "*Mesenchymal stem cells: environmentally responsive therapeutics for regenerative medicine,*" *Experimental & Molecular Medicine,* 45:e54 (2013)).

The primary trophic property of MSCs is the secretion of growth factors and other chemokines to induce cell proliferation and angiogenesis. MSCs express mitogenic proteins such as transforming growth factor-alpha (TGF-α), TGF-β, hepatocyte growth factor (HGF), epithelial growth factor (EGF), basic fibroblast growth factor (FGF-2) and insulin-like growth factor-1 (IGF-1) to increase fibroblast, epithelial and endothelial cell division. Vascular endothelial growth factor (VEGF), IGF-1, EGF and angiopoietin-1 are released to recruit endothelial lineage cells and initiate vascularization. It has been hypothesized that an individual's genotype has a role in the expression of and reaction to these cytokines, providing credence to the philosophy of personalized medicine utilizing responsive agents (that is, MSCs) rather than a dose of recombinant proteins or autologous growth factors (for example, plateletrich plasma). The trophic effects extend beyond cell proliferation to the reduction of scar tissue formation presumably by local cells secreting paracrine factors keratinocyte growth factor, stromal cell-derived factor-1 (SDF-1) and macrophage inflammatory protein-1 alpha and beta.

MSCs have been reported to possess anti-inflammatory and immunomodulatory properties. In many types of musculoskeletal trauma, inflammatory conditions at the site of injury impede the natural repair processes by local progenitor and mature cells. Without being bound by theory, it is believed that MSCs assist via paracrine mechanisms and modulate the regenerative environment via anti-inflammatory and immunomodulatory mechanisms. In response to inflammatory molecules such as interleukin-1 (IL-1), IL-2, IL-12, tumor necrosis factor-α (TNF-α) and interferon-gamma (INF-γ), MSCs secrete an array of growth factors and anti-inflammatory proteins with complex feedback mechanisms among the many types of immune cells. The key immunomodulatory cytokines include prostaglandin 2, TGF-β1, HGF, SDF-1, nitrous oxide, indoleamine 2,3-dioxygenase, IL-4, IL-6, IL-10, IL-1 receptor antagonist and soluble tumor necrosis factor-α receptor. MSCs prevent proliferation and function of many inflammatory immune cells, including T cells, natural killer cells, B cells, monocytes, macrophages and dendritic cells. Although MSCs across species are able to regulate T-cell activity, the mechanisms are not identical across mammalian species.

A characteristic of chronically inflamed environments is a persistent imbalance in the types of helper T cells and macrophages. MSCs indirectly promote the transition of TH1 to TH2 cells by reducing INF-g and increasing IL-4 and IL-10. The restored TH1/TH2 balance has been shown to improve tissue regeneration in cartilage, muscle and other soft tissue injuries, alleviate symptoms of autoimmune diseases and have an anti-diabetic effect. Similarly, reduction in INF-γ and secretion of IL-4 promotes a shift in macrophages from M1 (pro-inflammatory, anti-angiogenic and tissue growth inhibition) to M2 (anti-inflammatory, pro-remodeling and tissue healing) type, an effect required for skeletal, muscular and neural healing and regeneration. (See, Murphy, M. B., et al., "*Mesenchymal stem cells: environmentally responsive therapeutics for regenerative medicine,*" *Experimental & Molecular Medicine,* 45:e54 (2013)).

The foregoing cited publications, and all other publications cited throughout this application, are incorporated herein by reference in their entirety.

SUMMARY OF THE INVENTION

In one embodiment of the invention, the present application discloses an inventive method of treating inflammation associated with osteoarthritis of the knee joint by injecting mesenchymal stem cells into the symptomatic knee. In one aspect, the mesenchymal stem cells may be obtained autogenously. In another aspect, the osteoarthritis may be located in the medial tibial femoral joint of the knee. In yet another aspect, the mesenchymal stem cells are injected below the medial tibial plateau of the knee joint, resulting in alleviation of the symptoms of the osteoarthritis.

Accordingly, a broad object of particular embodiments of the invention herein can be to provide a method for treating inflammation associated with osteoarthritis of a knee resulting in alleviating symptoms of the osteoarthritis. The method includes obtaining mesenchymal stem cells, preferably autogenously; placing the mesenchymal stem cells into the tibial metaphysis of a tibia; reducing the inflammation, and alleviating the symptoms of osteoarthritis of the knee.

Another broad object of particular embodiments of the invention can be to provide a method for treating inflammation associated with osteoarthritis of a knee. The method includes obtaining mesenchymal stem cells, preferably autogenously; placing the mesenchymal stem cells into the tibial metaphysis of a tibia; reducing the inflammation, and regenerating the tibial metaphysis toward a normal physiologic structure.

Another broad object of particular embodiments of the invention can be to provide a method for alleviating symptoms of or treating osteoarthritis of a knee by treating inflammation associated with the osteoarthritis. The method includes obtaining bone marrow concentrate, preferably autogenously, which contains mesenchymal stem cells; placing the bone marrow concentrate containing the mesenchymal stem cells into one or more of the trabecular bone of the tibial metaphysis of the tibia below the tibial plateau and the medial tibial compartment of the knee.

Another broad object of particular embodiments of the invention can be to regenerate the tibial metaphysis of an osteoarthritic knee toward a normal physiologic structure by treating inflammation associated with the osteoarthritis. The method includes placing bone marrow concentrate, preferably obtained autogenously, which contains mesenchymal stem cells, into one or more of trabecular bone of the tibial metaphysis of said tibia below the tibial plateau and the medial tibial compartment of the knee.

In another broad object of embodiments of the invention, disclosed herein is a method of treating osteoarthritic knee joints by treating inflammation associated with the osteoarthritis. The method includes injecting mesenchymal stem cells (MSCs) into hyperemic or cystic subchondral bone in the osteoarthritic knee. In one aspect, the method comprises the use of autogenous bone marrow concentrate (BMC) that contains the MSCs, and injecting the BMC into the tibial metaphysis below the medial tibial plateau. In another aspect, the method comprises injecting both the medial knee joint and tibial metaphysis with the BMC.

In another broad object of embodiments of the invention, disclosed herein is a method of treating osteoarthritic knee joints by treating inflammation associated with the osteoarthritis. The method includes injecting MSCs into the tibial plateau, subchondral bone, or metaphysis in the osteoarthritic knee. In an alternative embodiment, the method comprises injecting the tibial plateau, subchondral bone, or metaphysis with bone marrow concentrate (BMC).

In another broad object of embodiments of the invention, disclosed herein is a method of treating an osteoarthritic knee joint by treating inflammation associated with the osteoarthritis. The method includes injecting hyperemic or cystic subchondral bone in the knee joint with MSCs or with BMC that contains the MSCs. Without being bound by theory, it is believed herein that the MSCs are anti-inflammatory and are able to differentiate into osteoblasts and thus reverse the hyperemic bone and fill the bone cysts with normal bone.

It is to be understood that, as contemplated herein, any suitable biologic MSC product may be utilized in the various embodiments of the invention disclosed herein. In a preferred embodiment, the biologic MSC product is BMC. BMC is an excellent source of MCSs, because the MSCs are stored in bone marrow. Illustrative examples of other sources from which MSCs may be isolated are peripheral blood, synovium, periosteum, skeletal muscle, and adipose tissue.

Many orthopedic surgeons believe that the pain of knee osteoarthritis is caused by abnormal stresses on the bone just beneath the tibial plateau. It has been reported that MRI scanning in patients who have medial osteoarthritis of the knee can show an isolated hyperemic area just beneath the tibial plateau in the tibial metaphysis. This hyperemic area on T2 weighted imaging is consistent with inflammation resulting in a localized area of increased bone blood flow. It has been reported that Surgeons have injected this area with various materials including bone cement and have used bone grafting of this area to decrease pain. In one embodiment of the invention herein, disclosed herein is a method of injecting a patient's medial tibial plateau with stem cells derived from bone marrow concentrate to help counter the abnormal pain inducing stress in this bone.

The use of BMC to obtain MSCs is standard of care in the veterinary world for the treatment of arthritic joints primarily in dogs and horses. Several prospective, randomized, double blind studies have been published indicating the efficacy of utilizing autogenous MSCs for the treatment of OA in dogs. Numerous other animal studies have been reported also verifying the efficacy of using BMC to place MSCs into animal arthritic joints. However, the primary problem in orthopedics is believed to be a lack of blood supply to the articular cartilage of a joint, and the ability of a cartilage cell to repair damage to the joint is very limited. Accordingly, in one embodiment of the invention herein, disclosed herein is an inventive method that utilizes a novel technique of injecting MCSs or BMC containing MCSs into an osteoarthritic knee joint of a human, resulting in treatment of the OA.

MSCs obtained from BMC have been reported to possess many positive attributes. MSCs are believed to be anti-inflammatory, secrete numerous growth factors, stimulate blood vessel formation, modulate the immune system to enhance healing, fight bacteria, and turn into cartilage cells to potentially heal an arthritic knee. Extensive research has been reported, showing efficacy of utilizing autogenous BMC with MCSs to treat osteoarthritis in animals and humans. However, to-date, this has never been successfully accomplished in treatment of osteoarthritic human knees. Accordingly, in one embodiment of the invention, disclosed herein is an inventive method that utilizes a novel approach for treatment of OA of the knee by injecting the tibial metaphysis below the degenerated medial tibial plateau of the knee joint. Without being bound by theory, it is believed that the MSCs in the BMC reduce the inflammation associated with osteoarthritis of the knee joint, will differentiate into osteoblasts, and will restore the damaged medial tibial metaphysis to a normal physiologic structure. In one aspect of this embodiment, the efficacy of BMC to treat knee OA is maximized by injecting both the knee joint and the medial knee joint and tibial metaphysis.

Naturally, further objects of the invention are disclosed throughout other areas of the specification, drawings, photographs, and claims.

DETAILED DESCRIPTION OF THE INVENTION

Before the present methods, implementations and systems are disclosed and described, it is to be understood that this invention is not limited to specific components, specific methods, specific implementation, or to particular compositions, and as such may, of course, vary. It is also to be understood that the terminology used herein is for the purpose of describing particular implementations only and is not intended to be limiting. Neither are mechanisms which have been provided to assist in understanding the disclosure meant to be limiting.

Figure 1:
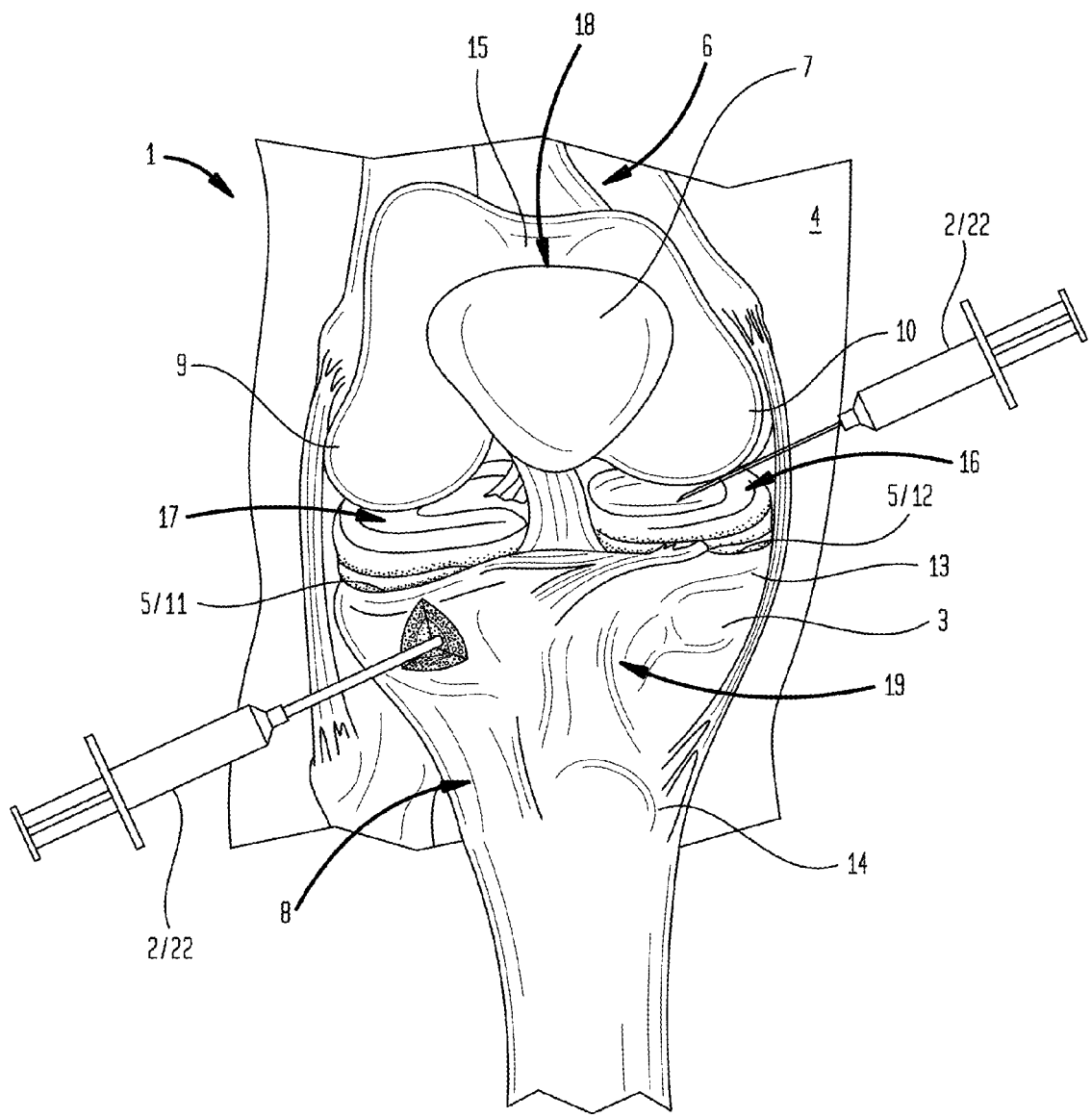
FIG. 1 is an illustration of a normal knee having certain structure removed to show the medial, lateral and patellofemoral compartments of the knee.

Now referring primarily to FIG. 1, disclosed herein is an inventive method of treating OA primarily of the medial tibial femoral joint (1) that involves treating inflammation that accompanies the OA. The method includes injecting mesenchymal stem cells ("MSCs") (2), preferably autogenous, into the medial tibial metaphysis (3) of the symptomatic knee (4) below the degenerated tibial plateau (5).

Referring again to FIG. 1, the knee joint (1) (also referred to herein as the medial tibial femoral joint) is comprised of three bones: the femur (the thigh bone) (6), the patella (the knee cap) (7), and the tibia (the shin bone) (8). The end of the femur (6) opposes the top of the tibia (8) to create the medial tibial femoral joint (1). Two round knobs called femoral condyles (9) (10) are found on the end of the femur (6). These condyles (9) (10) rest on the top surface of the tibia (8) (referred to herein as the "tibial plateau" (5)). The lateral half is referred to as the lateral tibial plateau (11), and the medial half is referred to as the medial tibial plateau (12). The medial tibial metaphysis (3) is the wide portion of the tibia (8) below the tibial plateau (5) between the tibial epiphysis (13) (the superior end part of the tibia (8)) and the tibial diaphysis (14) (the shaft or central part of the tibia (8)). The patella (7) glides through a special groove formed by the two femoral condyles (9) (10) called the patellofemoral groove (15). The knee joint (1) can be divided into a medial compartment (16) (the side of the knee (4) closest to the center of the body); the lateral compartment (17) (the side of the knee to the outside of the body); and the patellofemoral compartment (18) (the area behind the patella (7)).

Persons with OA of the medial tibial femoral joint (1) often point directly to this area of the knee (4) to describe their knee pain location and the medial tibial metaphysis (3) can be painful to palpation on physical examination. Consistent with observation on physical examination, magnetic resonance imaging ("MRI") of persons with OA of the medial tibial femoral joint (1) often show a hyperemic area (19) near the medial tibial metaphysis (3) on T2 weighted images which highlight differences in the T2 (spin-spin relaxation) time of tissues. Compressive forces during ambulation can be transferred through the medial tibiofemoral joint (1) to the tibial plateau (5) and the tibial metaphysis (3) which may result in or be a factor in causing OA of the medial tibial femoral joint (1).

In one embodiment of the invention, disclosed is a method for alleviating symptoms of osteoarthritis of a knee that includes treatment of inflammation that is associated with the osteoarthritis. The method comprises: (a) obtaining autogenous mesenchymal stem cells; (b) administering said autogenous mesenchymal stem cells into a tibial metaphysis of a tibia; and, (c) alleviating symptoms of said osteoarthritis of the knee. In one aspect, the method further comprises obtaining autogenous bone marrow concentrate containing said autogenous mesenchymal stem cells. In another aspect, the method further comprises aspirating autogenous bone marrow to obtain said autogenous bone marrow concentrate. Aspiration of said autogenous bone marrow results in obtention of about 5 milliliters to about 55 milliliters of said autogenous bone marrow concentrate. In another aspect, the method further comprises aspirating autogenous bone marrow of an ilium of a pelvis. In another aspect, administering of said autogenous mesenchymal stem cells into a tibial metaphysis of a tibia comprises injecting said autogenous mesenchymal stem cells into a trabecular bone of said tibial metaphysis of said tibia. This injecting of said autogenous mesenchymal stem cells may be carried out at a location of between about 1 centimeter to about 2 centimeters below the tibial plateau, and at a depth of between about 1 centimeter to about 2 centimeters. Injecting of said autogenous mesenchymal stem cells in any of the foregoing may comprise injecting an autogenous bone marrow concentrate containing said autogenous mesenchymal stem cells. This injecting of the autogenous bone marrow concentrate containing said autogenous mesenchymal stem cells may be carried out into said trabecular bone of said tibial metaphysis of said tibia. It further comprises injecting between about 5 milliliters to about 10 milliliters of said autogenous bone marrow concentrate containing said autogenous mesenchymal stem cells into said trabecular bone of said tibial metaphysis of said tibia, at a rate of about 1 milliliter per about 5 seconds to about 15 seconds, at a location of between about 1 centimeter to about 2 centimeters below the tibial plateau, and at a depth of between about 1 centimeter to about 2 centimeters. In another aspect, the method of any of the above further comprises plugging the entry spot of injection into said tibia.

In another embodiment, the above method may further comprise injecting said autogenous mesenchymal stem cells into a medial tibial compartment of said knee. In one aspect, this method comprises injecting autogenous bone marrow concentrate containing said autogenous mesenchymal stem cells into said tibial metaphysis of a tibia and said medial tibial compartment of said knee. In another aspect, this comprises injecting about 5 milliliters to about 10 milliliters of said autogenous bone marrow concentrate containing said autogenous mesenchymal stem cells into each of said tibial metaphysis of a tibia and into said medial tibial compartment of said knee. In another aspect, this comprises injecting between said about 5 milliliters to about 10 milliliters of said autogenous bone marrow concentrate containing said autogenous mesenchymal stem cells into said trabecular bone of said tibial metaphysis of said tibia at a rate of about 1 milliliter per about 5 seconds to about 15 seconds. In another aspect, the method in any of the foregoing comprises regenerating said tibial metaphysis toward a normal physiologic structure.

In another embodiment of the invention, disclosed is a method for treating osteoarthritis of the knee that includes treatment of inflammation that is associated with the osteoarthritis. The method comprises: (a) obtaining autogenous mesenchymal stem cells; (b) injecting said autogenous mesenchymal stem cells into a tibial metaphysis of a tibia; and, (c) regenerating said tibial metaphysis toward a normal physiologic structure. In one aspect, the method further comprises obtaining autogenous bone marrow concentrate containing said autogenous mesenchymal stem cells. The method further comprises aspirating autogenous bone marrow to obtain said autogenous bone marrow concentrate. The method further comprises aspirating said autogenous bone marrow to obtain about 5 milliliters to about 55 milliliters of said autogenous bone marrow concentrate. The method further comprises aspirating autogenous bone marrow of an ilium of a pelvis. The method further comprises processing the bone marrow as described in Pettine, K. A., U.S. Pat. No. 9,408,874 (Aug. 9, 2016), which is incorporated herein by reference in its entirety. The method further comprises injecting said autogenous mesenchymal stem cells into a trabecular bone of said tibial metaphysis of said tibia. The method further comprises injecting said autogenous mesenchymal stem cells into said trabecular bone of said tibial metaphysis of said tibia at a location of between about 1 centimeter to about 2 centimeters below the tibial plateau, at a depth of between about 1 centimeter to about 2 centimeters. The method further comprises injecting said autogenous mesenchymal stem cells into a trabecular bone of said tibial metaphysis of said tibia at a depth of between about 1 centimeter to about 2 centimeters. The method further comprises injecting said autogenous mesenchymal stem cells into said trabecular bone of said tibial metaphysis of said tibia at a location of between about 1 centimeter to about 2 centimeters below the tibial plateau. The method of any of the foregoing further comprising injecting an autogenous bone marrow concentrate containing said autogenous mesenchymal stem cells. The method further comprises injecting autogenous bone marrow concentrate containing said autogenous mesenchymal stem cells into said trabecular bone of said tibial metaphysis of said tibia; which further comprises injecting between about 5 milliliters to about 10 milliliters of said autogenous bone marrow concentrate containing said autogenous mesenchymal stem cells into said trabecular bone of said tibial metaphysis of said tibia; which further comprises injecting between said about 5 milliliters to about 10 milliliters of said autogenous bone marrow concentrate containing said autogenous mesenchymal stem cells into said trabecular bone of said tibial metaphysis of said tibia at a rate of about 1 milliliter per about 5 seconds to about 15 seconds; which further comprises injecting said autogenous mesenchymal stem cells into said trabecular bone of said tibial metaphysis of said tibia at a location of between about 1 centimeter to about 2 centimeters below the tibial plateau; which further comprises injecting said autogenous mesenchymal stem cells into a trabecular bone of said tibial metaphysis of said tibia at a depth of between about 1 centimeter to about 2 centimeters. In one aspect, the method of any of the above further comprises plugging said entry spot of injection into said tibia. In another aspect, the method of any of the above further comprises injecting said autogenous mesenchymal stem cells into a medial tibial compartment of said knee. In another aspect, the method of any of the above further comprises injecting autogenous bone marrow concentrate containing said autogenous mesenchymal stem cells into said tibial metaphysis of a tibia and said medial tibial compartment of said knee; which further comprises injecting about 5 milliliters and about 10 milliliters of said autogenous bone marrow concentrate containing said autogenous mesenchymal stem cells into each of said tibial metaphysis of a tibia and into said a medial tibial compartment of said knee; which further comprises injecting between said about 5 milliliters to about 10 milliliters of said autogenous bone marrow concentrate containing said autogenous mesenchymal stem cells into said trabecular bone of said tibial metaphysis of said tibia at a rate of about 1 milliliter each about 5 seconds to about 15 seconds. In another aspect, the method in the foregoing comprises alleviating symptoms of said osteoarthritis of the knee.

The use of BMA (bone marrow aspirate) and BMC (bone marrow concentrate) are known to contain hematopoietic as well as MSC populations. The method of extraction is typically correlative to the source of these cells. Typically, the novel technology utilizes an approach, whereby approximately 10 cc of BMA is drawn with typically frequent rotation and repositioning. Additional draws are done after deeper placement of a needle in the iliac crest.

Bone marrow collection and processing to BMC is carried out herein as described in Pettine, K. A., U.S. Pat. No. 9,408,874 (Aug. 9, 2016), which is incorporated herein by reference in its entirety. This provides a pre-determined amount of a processed bone marrow concentrate with a pre-determined amount of a pre-mixture, where the pre-mixture includes quantities of anticoagulant solution, dextrose and phosphate buffered saline. Typically, the iliac crest, and more typically the posterior iliac crest, is where bone marrow aspirate may be harvested in a surgical setting, however any suitable area where BMA may be extracted may be used. The novel cellular "snapshot" is derived via timely methodologies specific to non-expanded, minimally manipulated, autologous cell and associated endogenous microenvironment ("milieu"). Typically, once extracted, the BMA and the resulting BMC is obtained by isolation of the desired cell populations via centrifugation. However, any suitable means may be used to obtain the BMC from the BMA. When centrifugation is used, the BMA is separated according to the slightly differing specific gravities of the aspirated cell types. The cells contained in the BMA can be stratified under centrifugation. The volume, rate, and time of centrifugation are important for controlling the resulting biologic factors contained within the endogenous milieu. Typically, the longer the processing time and/or the more agitation and handling, the lower the oxygen level in the extracted cells which typically include cellular constituents and components sequestered in the residual endogenous milieu, wherein the milieu typically includes, antigens, surface biomarkers, proteins and growth factors for angiogenesis, osteogenesis, other regenerative outcomes, and the like. In some embodiments, the degradative manipulation and resultant influence during processing is limited. The resulting, unadulterated milieu may retain a large number of unchanged biologic drivers, markers and signals that are dose appropriate and specific to the cascade of healing found through the native physiology. The stratification and selection of MSCs and progenitors from this population may influence traits such as specific plasticity and immunomodulation. Typically, the time between extraction and re-implantation is within 1 hour, and more typically within 30 minutes, and still more typically within 20 minutes. Thus, a point of care approach may be typically implemented with the novel technology. Optionally, once the BMA has been centrifuged, the resulting stratified cell layers may be prepared for delivery to the patient. Typically, the containers, anticoagulants used, and the delivery media used for interim storage and delivery are also prepared during this step. In some embodiments, preserving endogenous proteins, structure and morphology resides within this step, as too great a deviation from the oxygen, microenvironment and stress factors can lead to changes in the composition of the milieu. Typically, the proteins, structure, and morphology are not significantly altered. In one embodiment, the novel delivery media formulation is tailored to preserve the extracted cells and their endogenous factors, while maintaining cell health and identity. Typically, a premixture including an aqueous solution of anticoagulant (ACD-A), an equal amount of dextrose (50%), and phosphate buffered saline (PBS), or the like is pre-mixed and aliquoted in a volume to typically match or approximate the cellular matrix extracted from the centrifugation stratification layers at a ratio of about 1:1. More typically, the premixture is added to the cellular matrix with specific volumes being matched to, or slightly greater than 50/50, by volume, although the ratio may be greater, such as 2:1 or even higher. In some embodiments, the steps in extracting, isolating, separating, re-extracting, dosing, mixing, and delivery impact the cell population, endogenous proteins, surface structural and biomarkers, associated with the compositional regenerative capacity. Typically, the shorter the time consumed by the above mentioned steps, the less adulterated the original milieu composition will become.

EXAMPLES

The following examples further illustrate specific embodiments of the invention. However, the following examples should not be interpreted in any way to limit the invention.

Example 1. Procedures and Materials

Various procedures can be used to evaluate, classify and measure the severity of OA of the medial tibial femoral joint (1).

Lower Extremity Functional Scale ("LEFS").

LEFS is a questionnaire containing 20 questions about a person's ability to perform tasks. The LEFS can be used by clinicians as a measure of patients' initial function, ongoing progress and outcome, as well as to set functional goals. (Binkley J M, Stratford P W, Lott S A, Riddle D L, "*The Lower Extremity Functional Scale (LEFS): scale development, measurement properties, and clinical application*", North American Orthopaedic Rehabilitation Research Network, *Phys Ther.* 1999 Apr. 1979 (4):371-83). The LEFS can be used to evaluate the functional impairment of a person with a disorder of one or both lower extremities. It can also be used to monitor the patient over time and to evaluate the effectiveness of an intervention.

Each of the 20 questions is scored on a scale having five grades:
Grade 0: Extreme difficulty or unable to perform activity.
Grade 1: Quite a bit of difficulty
Grade 2: Moderate difficulty.
Grade 3: A little bit of difficulty.
Grade 4: No difficulty.

The columns on the scale are summed to get a total score. The maximum score is 80. The lower the LEFS score the greater the disability. The minimal detectable change is 9 scale points. The minimal clinically important difference is 9 scale points. Percent of maximal function=(LEFS score)/80×100.

Visual Analog Scale (VAS).

VAS is a measurement instrument that measures the amount of pain that a person perceives across a continuum from none to an extreme amount of pain. Operationally, a VAS usually takes the form of a horizontal line, 100 mm in length, anchored by word descriptors at each end. The person marks on the line the point that represents their perception of their current state. The VAS score is determined by measuring in millimeters from the left-hand end of the line to the point that the patient marks. (Journal of Clinical Nursing, 10, 697-706).

Kellgren and Lawrence System ("K/L System").

The K/L system is a method of classifying the severity of radiographic knee OA based on a scale having five grades. (Kellgren, J. H.; Lawrence, J. S. (1957), "Radiological assessment of osteo-arthrosis," Annals of the Rheumatic Diseases 16 (4):494-502).

The five grades of the K/L system include:
Grade 0: no radiographic features of OA are present.
Grade 1: doubtful joint space narrowing (JSN) and possible osteophytic lipping.
Grade 2: definite osteophytes and possible JSN on antero-posterior weight-bearing radiograph.
Grade 3: multiple osteophytes, definite JSN, sclerosis, possible bony deformity.
Grade 4: large osteophytes, marked JSN, severe sclerosis and definite bony deformity.

The more recently developed Osteoarthritis Research Society International (OARSI) atlas criteria may also be utilized to classify the severity of radiological knee OA. (Altman, R D, Gold, G E (2007) "*Atlas of individual radiographic features in osteoarthritis*," revised, *Osteoarthr Cartil* 15:A1-A56; Altman, R D, Hochberg, M, Murphy, W A Jr, Wolfe, F, Lequesne, M (1995) *Atlas of individual radiographic features in osteoarthritis*).

Figure 2:
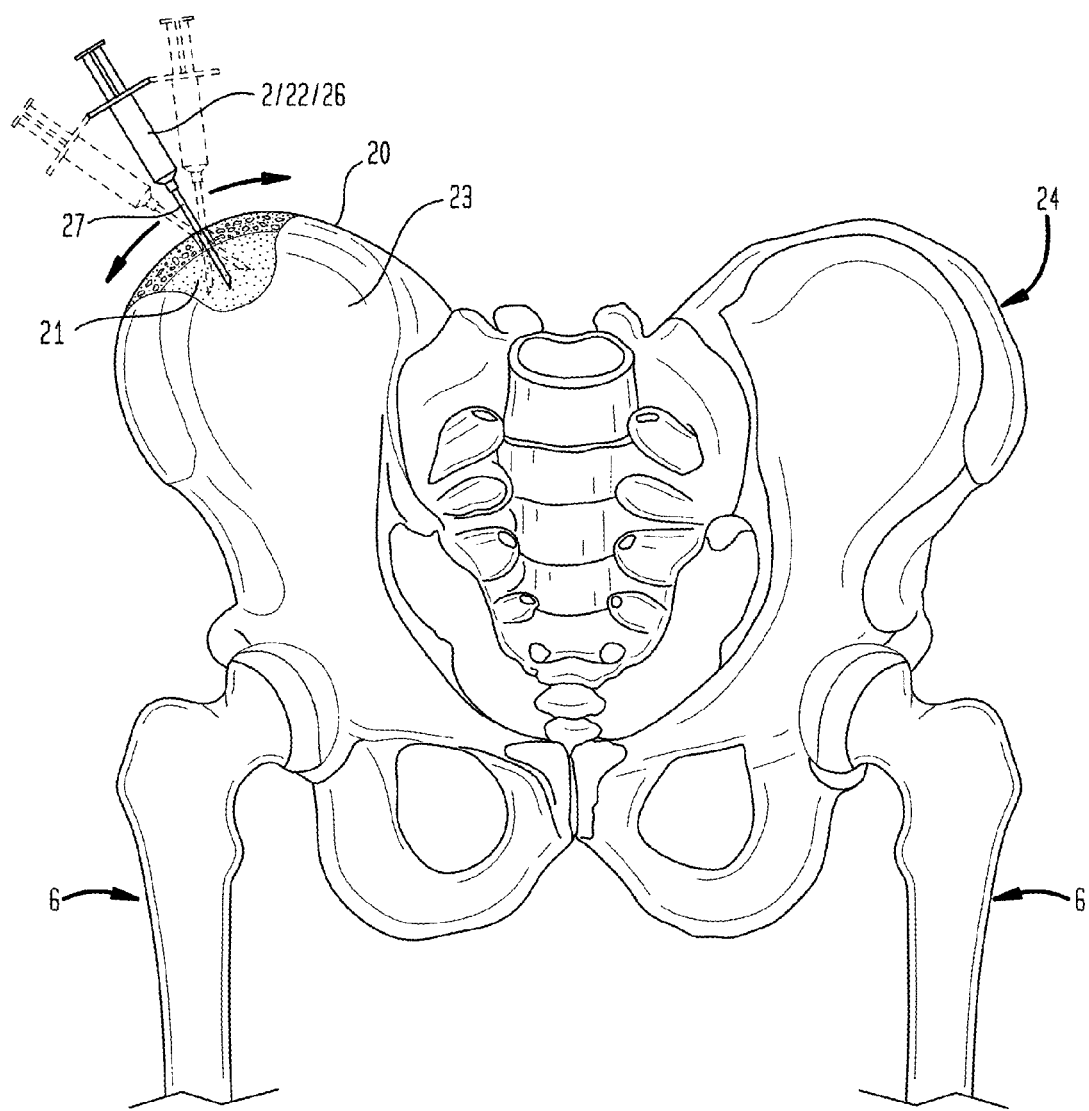
FIG. 2 is an illustration of the pelvic girdle showing a needle advanced through the iliac crest and into bone marrow to aspirate bone marrow from the ilium.

Now referring primarily to FIG. 2, autogenous MSCs (2) are multipotent stromal cells that can differentiate into a variety of cell types, including: osteoblasts (bone cells), chondrocytes (cartilage cells), myocytes (muscle cells) and adipocytes (fat cells). Autogenous MSCs (2), suitable for use in embodiments of the inventive method, are typically obtained from bone marrow (22) or fractions thereof; however, this is not intended to limit obtention of autogenous MSCs (2) suitable for use with the inventive method solely from bone marrow (21) and it is understood that autogenous MSCs (2) may be isolated from other tissues such as: peripheral blood, synovium, periosteum, skeletal muscle, or adipose tissue. Additionally, as to certain embodiments, it is understood that autogenous MSCs (2), whether from bone marrow (21) (or fractions thereof) or other tissue sources, can be expanded in media to obtain an amount of autogenous MSCs (2) for use in embodiments of the inventive method.

Typically, bone marrow aspirates can have a cellularity of marrow (21) of about 15 to about 30 million mononuclear cells per milliliter ("MNC/mL"), whereas less than 10 million MNC/mL usually means a rather diluted sample provided the donor was healthy and the marrow not fibrotic. The average colony forming unit-fibroblasts ("CFU-f") content of healthy human bone marrow is about 100 CFU-f/million MNC. Accordingly, bone marrow concentrate (22) ("BMC") resulting from aspirating bone marrow (21) (as shown in the example of FIG. 2) can contain a few thousands (about 1500 to about 3000) CFU-f/mL of bone marrow (21).

As to certain embodiments, there may be an advantage in pooling 3 to 4 separate aspirations (around 15-20 mL total) of bone marrow (21). The pooled aspirates of the bone marrow (21) can be diluted in cell culture medium (using platelet lysate instead of fetal bovine serum) and seeded directly into culture vessels without any further purging or manipulation. Non-adherent cells can be removed between 48 to 72 hours. First passage (P1) autogenous MSCs (20) meet the MSC criteria of the International Society for Cellular Therapy. This protocol can yield several hundred millions of autogenous MSCs (2) from the original aspirated bone marrow (21) within a few weeks.

As to particular embodiments, autogenous MSCs (2) obtained from bone marrow (21) can be utilized in embodiments of the inventive method as autogenous BMC (22)

without further processing; although autogenous MSCs (2) can be contained or entrained in other injectable or otherwise administratable biocompatible materials or compositions such as biocompatible hydrogels, or the like. One source of autogenous BMC (22) can be the bone marrow (21) of the ilium (23) of the greater pelvis (24); although autogenous BMC (22) obtained from other sites may be utilized.

Now referring primarily to FIGS. 1 and 3, autogenous MSCs (2) can be injected or otherwise administered in accordance with embodiments of inventive method into one or more of: the trabecular bone (25) of the medial tibial metaphysis (3) below the degenerated tibial plateau (5), the medial compartment (16) of the knee (4), or the lateral compartment (17) of the knee (4) causing the autogenous MSCs (2) contained in the autogenous BMC (22) or biocompatible material or composition to differentiate into osteoblasts or chondrocytes to alleviate symptoms of OA or to treat OA by regeneration of the damaged medial tibial metaphysis (3) toward or to a normal physiologic structure.

Figure 3:
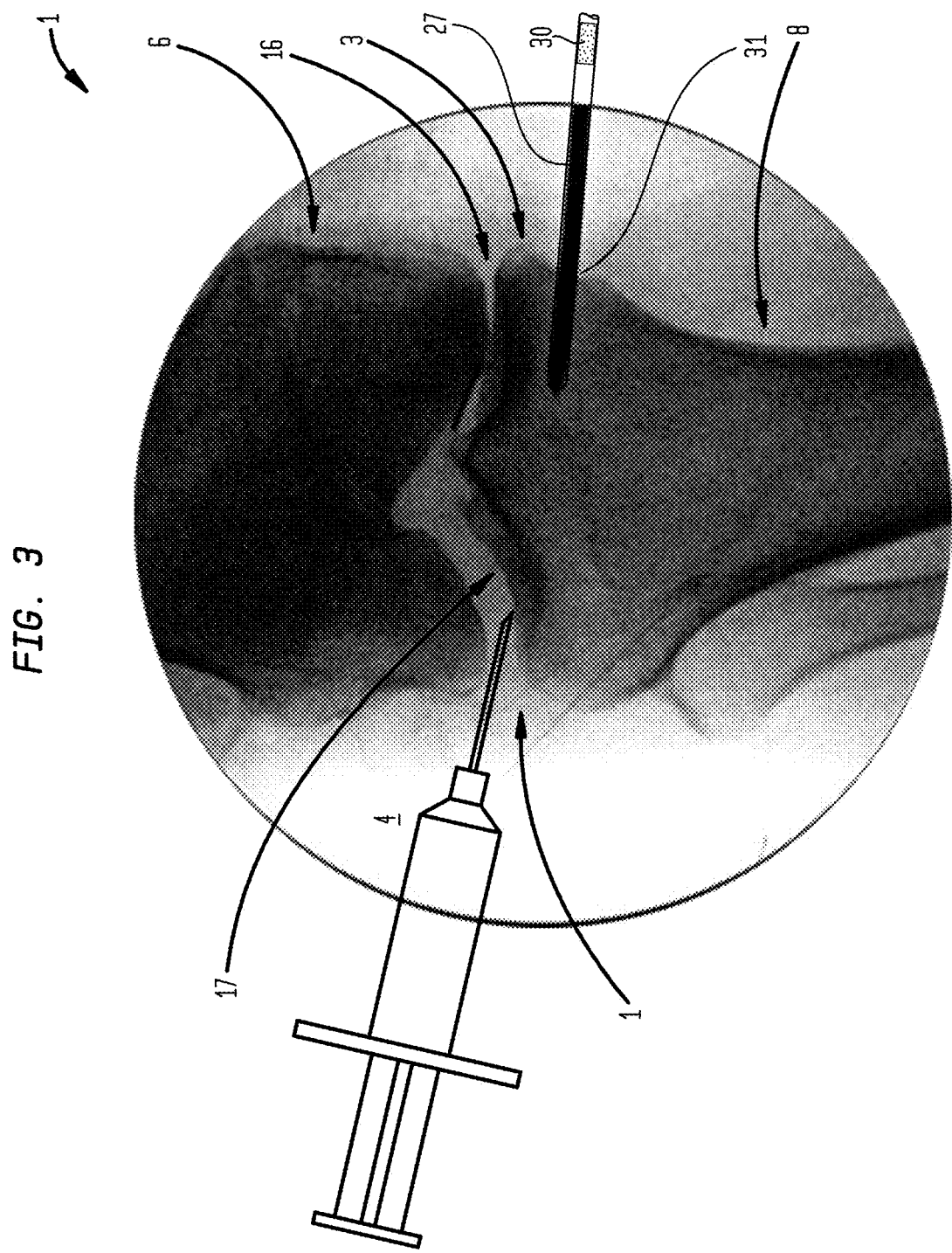
FIG. 3 is a fluoroscopy image of a particular embodiment of the inventive method for alleviating symptoms of and treating osteoarthritis of the knee showing the needle position used in injecting biocompatible materials containing autogenous mesenchymal stem cells or autogenous bone marrow concentrate into the knee for treating medial osteoarthritis of the knee with a larger needle advanced through the cortical bone into the trabecular bone and the smaller needle advanced into the medial compartment of the knee.

As to particular embodiments, autogenous MSCs (2) can be injected or otherwise administered into the trabecular bone (25) of the tibial metaphysis (3) of the tibia (8) at a location of between about 1 centimeter to about 2 centimeters below the tibial plateau (5) at a depth into the trabecular bone (25) of about 1 centimeter to about 2 centimeters (as shown in the example of FIG. 3). As to particular embodiments, the autogenous MSCs (2) can be injected or administered in the form of autogenous BMC (22), or the autogenous MSCs (2) can be contained in other biocompatible materials or compositions injectable or otherwise administrable into the trabecular bone (25) of the tibial metaphysis (3). The volume or amount autogenous BMC (22) or biocompatible material or composition containing or entraining similar or greater numbers of autogenous MSCs (2) injected or otherwise administered into the trabecular bone (25) can be an amount of between about 5 milliliters and about 10 milliliters. The amount of autogenous BMC (22) or biocompatible material or composition containing autogenous MSCs (2) can be injected or administered into the trabecular bone (25) of the tibial metaphysis (3) at a rate of about 1 milliliter per each 5 seconds to about 15 seconds to allowing dispersion of the autogenous BMC (22) or biocompatible material or composition containing autogenous MSCs (0) within the trabecular bone (25).

Embodiments of the inventive method can be used to alleviate symptoms of OA of the knee (4) such as stiffness, pain, or swelling or can be used to treat OA of the knee (4) including regenerating the tibial metaphysis (3) toward or to a normal physiologic structure.

Example 2: Technique for Treatment of Inflammation in an Osteoarthritic Knee Joint Resulting in Reduction of the Osteoarthritis The following is a technique used to maximize the biologic treatment of medial osteoarthritis of the knee joint by treatment of the inflammation associated with the osteoarthritis. The technique involves the following. Any biologic mesenchymal stem cell product can be utilized. The patient's physical examination must be consistent with the following. They must have pain primarily along the medial side of the knee and specifically the proximal tibial plateau or metaphyseal area of the tibia with palpation. On examination, the knee will often have a pseudomedial laxity of the medial tibial femoral joint and be in a genu varum alignment. Radiographs reveal either a Kellgren grade-3 or grade-4 change specific to the medial tibiofemoral joint. MM scanning will show a hyperemic area beneath the medial joint space and the tibial metaphysis on a T2 weighted image. These conditions must all be present.

At this point, the knee is prepped with betadine. The medial skin, approximately a centimeter below the medial joint space and centered anteriorly posteriorly on the lateral view of the knee, is anesthetized with buffered 1% xylocaine, with a 25-gauge needle. At this point, a JAMSHIDI® bone marrow biopsy needle is placed in the mid-point anteriorly, posteriorly of the tibial metaphysis on the lateral view and a centimeter below the joint space on the anterior, posterior view. With a mallet the JAMSHIDI® needle is directed such that its tip is a centimeter below the joint space on the anterior, posterior view and between 1.5 to 2 centimeters from the medial side of the tibial metaphysis. At this point, 5 mL of biologic material is placed through the JAMSHIDI® needle to fill the interstices of the tibial metaphysis. A plug of bone wax is placed through the JAMSHIDI® needle to plug the entry spot into the bone to prevent back leakage of the biologic material. The biologic is introduced slowly through a 5 mL syringe at a rate of 1 mL for every 10 seconds of delivery. This assures even distribution of the biologic into the target area and keeps interstitial pressure to a minimum to decrease the pain involved with the injection. An additional 5 to 10 mL of the biologic is then placed into the knee joint itself to complete the technique. Because of the synovial lining of the knee, the biologic material will stay within the knee.

Example 3: Detailed Treatment of Inflammation in an Osteoarthritic Knee Joint Resulting in Reduction of the Osteoarthritis A prospective open-label non-randomized case series evaluation was performed utilizing autogenous BMC (22) for the treatment of medial compartment (16) OA of the knee (4). The primary objective of the study was to determine the safety and feasibility of performing an intra-articular injection or injection into the medial tibial metaphysis (3) of autogenous BMC (22) containing autogenous MHCs (2) into the symptomatic 20 knee (4) to treat medial compartment (16) OA. Secondary objectives were: 1) to evaluate the effectiveness of autogenous BMC (22) in improving function and limiting disability as measured by the lower extremity functional scale ("LEFS"); 2) to evaluate improvements in pain as assessed using a visual analog score ("VAS") for pain; 3) to evaluate the effectiveness of autologous BMC (22) in reducing the need for surgical intervention out to one year post-treatment; and, 4) to provide preliminary data to support autogenous BMC (22) for future studies. The study was performed at a single center.

PARTICIPANTS: All of the study participants complained of knee (4) pain consistent with medial compartment (16) OA of the knee (4). OA was defined by pain and stiffness in the medial side of the knee (4) worsened with exercise and weight bearing. All participants underwent a pre-treatment medical history and physical examination of their knee (4) including a LEFS score and VAS pain score. In addition, all participants had standing anteroposterior ("AP") and lateral radiographs as well as MM scanning. Standing radiographs were utilized to rate the participants on the K/S scale as 0, 1, 2, 3, or 4. Follow up was obtained at three months, six months, and twelve months following the treatment.

All participants had radiographic evidence of at least grade-3 or grade-4 medial tibial femoral osteoarthritis severity based on the K/S scale. There were thirteen participants with K/S grade-4 medial tibial femoral osteoarthritis, and ten participants with K/S grade-3 medial tibial femoral osteoarthritis. K/S grade-3 medial tibial femoral osteoarthritis is moderate to severe and K/S grade-4 medial tibial femoral osteoarthritis is severe, often bone on bone wear. In patients with bilateral medial OA, both knees (4) were treated in accordance with the inventive method of treatment.

BONE MARROW COLLECTION AND PROCESSING: Following is a first illustrative example of bone marrow collection and processing to BMC, which was carried out as described in Pettine, K. A., U.S. Pat. No. 9,408,874 (Aug. 9, 2016), which is incorporated herein by reference in its entirety. Accordingly, 60 cc of bone marrow aspirate was collected over ACD-A as needed per process. The marrow was processed using the bone marrow concentration system according to the detailed protocol. The patient was given IV antibiotics and placed prone on an image table. Intravenous Versed and Fentanyl was administered and the skin was anesthetized with buffered 1% Lidocaine. The aspirator was rinsed and the syringes were transferred with heparin solution, approximately 1000 U/ml. The heparin solution coated the inner surface of the 60 cc aspiration needle and trephine needle. The remaining heparin was expelled from the syringe. 6 cc of ACD-A was aspirated into the 60 cc syringe. Bone marrow was aspirated from the posterior iliac crest when the patient was positioned prone on a fluoro table. The right iliac wing was prepped and draped according to standard surgical protocols. A trephine needle and 60 cc syringe was used to remove the marrow. The surgeon inserted the trephine needle percutaneously through the skin until the bony surface of the iliac crest was felt. Using a mallet, the needle was then inserted to a depth of 3-4 cm into the crest. This was accomplished with fluoroscopic guidance. A 60 cc syringe containing 6 ml of acid citrate dextrose anticoagulant solution (ACD-A) (10% of the final volume) was attached to the needle. The marrow was aspirated by pulling the plunger back and allowing the syringe to fill to the 10 cc level. The needle was repositioned by advancing 1.5-2 cm and an additional 10 cc of aspirate was obtained. This process was repeated until 60 cc of iliac aspirate was obtained. Once the final marrow volume was reached, the solution was mixed by gentle rocking of the syringe as the syringe was rotated on its long axis. The marrow was then ready for processing. The marrow was mixed anticoagulant solution by gently turning the syringe after each 10 cc of aspirate collection. The extracted marrow was placed in an isolating canister and loaded into the centrifuge. The marrow was centrifuged for 12 minutes at 3200 rpm. The processed marrow was drawn with a syringe from the centrifuge and then rocked while rotating the syringe on its long axis. The syringe was then presented to a sterile field. The amount of bone marrow concentrate removed from the centrifuge equaled the amount to be injected. The cell delivery media was pre-mixed and aliquoted to 1 cc, composing of 0.5 cc of ACD-A and 0.5 cc of dextrose (50%). The delivery media was injected into a closed vial containing the cell components slowly, in order to homogenize the mixture and incorporate oxygen and turbidity mixing in a closed, sterile system.

Following is a second illustrative example of bone marrow collection and processing to BMC. Now referring primarily to FIG. 2, about 55 milliliters ("mL") of autogenous bone marrow aspirate (26) ("BMA") was collected over about 5 mL acid citrate dextrose-anticoagulant ("ACD-A") from the participant's posterior iliac crest (20) of the ileum (23) of the greater pelvis (24). The procedure was performed with intravenous sedation consisting of VERSED® (also known as Midazolam) (8-chloro-6-(2-fluorophenyl)-1-methyl-4H-imidazo[1,5-a]-[1,4]benzodiazepine, CAS Number: 59467-70-8) and FENTANYL® (N-(1-(2-phenylethyl)-4-piperidinyl)-N-phenylpropanamide, CAS Number 437-38-7). Positioning of a JAMSHIDI® bone marrow biopsy needle (27) in the iliac crest (20) was confirmed by fluoroscopy. BMA (26) was collected in a 60 mL syringe in a series of discrete pulls on the plunger (targeting a collection of 5-10 mL per pull), with repositioning of the needle tip between pulls based on the reported enrichment of autogenous MSCs (20) as described by Hernigou, et al., *J Bone Joint Surg Br* 2005 87 (7) 896-902. The BMA (26) was captured using a ART21® BMC cell capturing device available from Celling Biosciences, Austin, Tex. to obtain BMC (22). Typically, a BMC (22) volume of about 12 mL (about 6 mL for injection into the medial or lateral tibial metaphysis (3) and about 6 mL for injection into the medial compartment (16)) was drawn from the ART21° BMC cell capturing device.

KNEE INJECTION: Now referring primarily to FIGS. 1 and 3, participant's knee skin was sterilized with BETADINE® (2-pyrrolidinone, 1-ethenyl-, homopolymer, compound with iodine; CAS Number: 25655-41-8). Under fluoroscopic control, a 20 gauge needle (28) was placed medial to the anterior parapatellar tendon (28) into the medial compartment (16). Needle (28) placement was verified with fluoroscopy as shown in the example of FIG. 3. At this point, about 6 mL of autogenous BMC (22) was placed into the medial compartment (16) of the knee joint (1). Following this, the medial skin about 1.5 centimeters ("cm") below the tibial plateau (5) was anesthetized with buffered 1% Xylocaine (2-(diethylamino)-N-(2,6-dimethylphenyl)acetamide, CAS Number: 137-58-6). A JAMSHIDI® bone marrow biopsy needle (27) was then advanced through the cortical bone (29) to between about 1 cm to about 2 cm into the medial or lateral tibial metaphysis (3) and between about 1 cm and about 2 cm below the tibial plateau (5). The bone marrow biopsy needle (27) was then placed about midline anterior posterior of the tibia (8) with the bone marrow biopsy needle (27) placement verified under fluoroscopic control as shown in the example of FIG. 3. At this point, about 6 mL of autogenous BMC (22) was slowly delivered (about 1 mL per each 10 seconds) into the trabecular bone (25) of the medial tibial metaphysis (3). This allowed more even distribution of the autogenous BMC (22) into the tibial metaphysis (3). A plug (30) of bone wax (CAS NO:8021-48-5) was placed through the JAMSHIDI® bone marrow biopsy needle (27) to plug the needle entry spot (31) into the tibia (8) and reduce or prevent back leakage of the autogenous BMC (22).

POST INJECTION: Participants were prescribed pain medication to be used as needed for three days. Participants had restricted physical activity for two weeks following the procedure. Passive low resistant range of motion was encouraged immediately. At two weeks, the participants were allowed to return to full activities.

Figure 4:
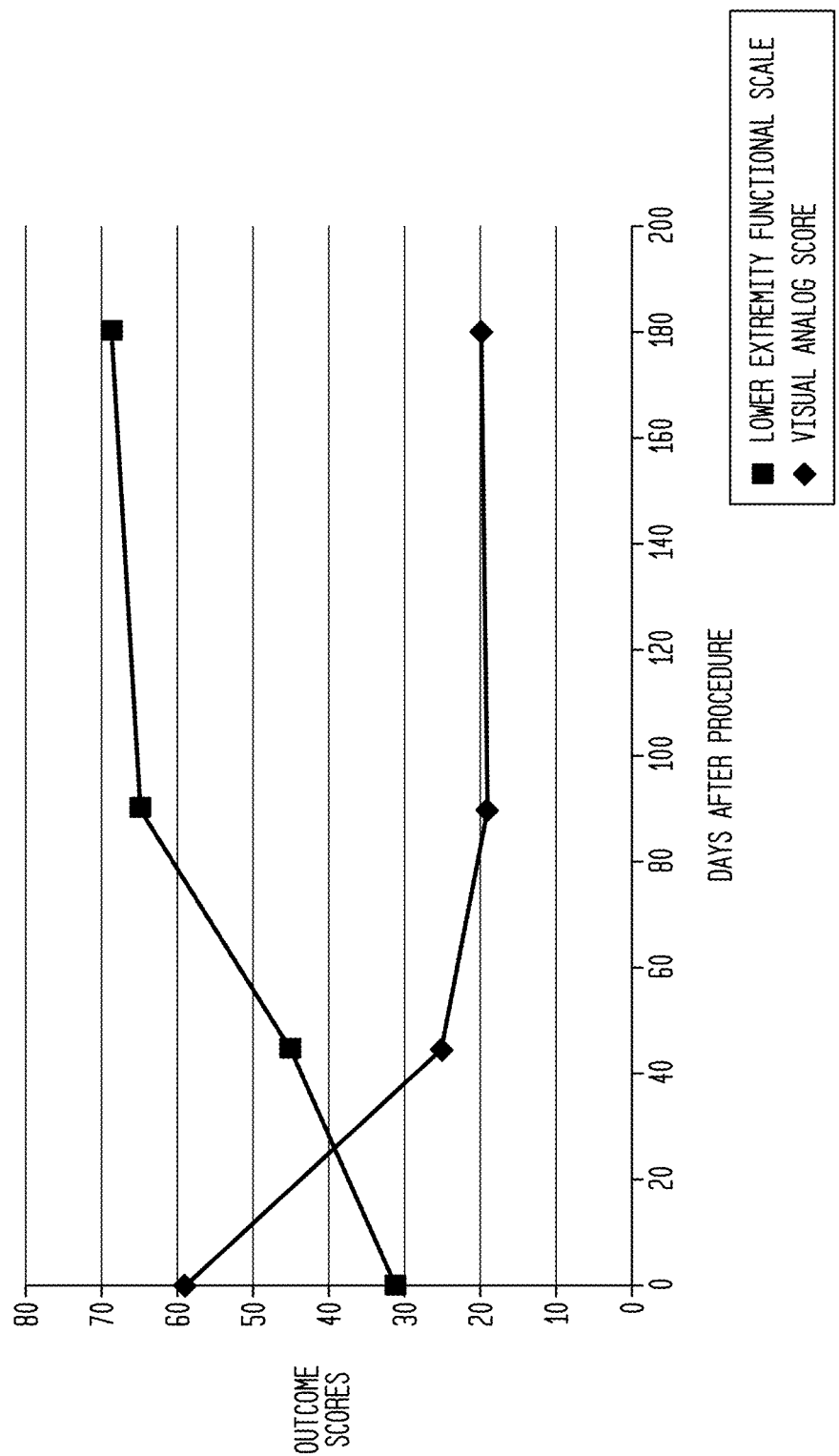
FIG. 4 is a plot of participant reported VAS and LEFS score averages at 6 weeks, 3 months and 6 months post treatment with the inventive method evidencing alleviation of symptoms of osteoarthritis of the knee.

RESULTS: Now referring primarily to FIG. 4, participants were monitored for adverse events through a mean four months of follow up. Several participants (8/23), most between 3 and 5 6 months post procedure, reported pain at or below a 20 VAS score. Of the patients treated only 4 had VAS pain scores above 30. There were significant improvements in LEFS as well, with the average LEFS score (out of 80, with 80 being no limitation/disability and 0 being complete disability) improving from a 31 LEFS score at baseline to a 58 LEFS score at mean 4 months follow-up. The average VAS score dropped from 61 at baseline to a VAS score at follow-up. There were no serious adverse events reported, and no patient reported increases in pain or disability (VAS and LEFS score). Patients with at least 6 months of follow-up had average LEFS score of 69 and an average VAS score of 20.

It is to be understood that, as contemplated herein, in any and all instances throughout this application where Applicants refer to injection(s) using BMC and/or MSC, any and all of the various BMC and/or MSC delivery media or mixtures described herein may be used, whether the specific details of the BMC and/or MSC delivery media or mixture are recited or not.

As can be easily understood from the foregoing, the basic concepts of the present invention may be embodied in a variety of ways. The invention involves numerous and varied embodiments of a treatment of inflammation associated with medial or lateral osteoarthritis of the knee with autogenous mesenchymal stem cells (2y) including the best mode resulting in reduction of the osteoarthritis.

As such, the particular embodiments or elements of the invention disclosed by the description or shown in the figures or tables accompanying this application are intended to be exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "treatment" should be understood to encompass disclosure of the act of a "treating", whether explicitly discussed or not, and, conversely, were there effectively disclosure of the act of "treating", such a disclosure should be understood to encompass disclosure of a "treatment" and even a "means for treating." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition each definition hereby incorporated by reference.

All numeric values herein are assumed to be modified by the term "about", whether or not explicitly indicated. For the purposes of the present invention ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes, for example, the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) a treatment of medial or lateral osteoarthritis of the knee with autogenous mesenchymal stem cells herein disclosed and described, ii) the related methods disclosed and described, iii) similar equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

While the disclosure has been illustrated and described in detail in the figures and foregoing description, the same is to be considered as illustrative and not restrictive in character, it being understood that only selected embodiments have been shown and described and that all changes, modifications and equivalents that come within the spirit of the disclosures described heretofore and/or defined by the following claims are desired to be protected. In addition, all publications cited herein are indicative of the level of skill in the art and are hereby incorporated by reference in their entirety as if each had been individually incorporated by reference and fully set forth.

What is claimed is:

1. A method for treating inflammation in an osteoarthritic knee to alleviate the osteoarthritis, comprising:
   (a) obtaining autogenous mesenchymal stem cells;
   (b) administering said autogenous mesenchymal stem cells into a tibial metaphysis of a tibia;
   (c) reducing the inflammation; and,
   (d) alleviating symptoms of said osteoarthritis in the knee.

2. The method of claim 1, further comprising obtaining autogenous bone marrow concentrate containing said autogenous mesenchymal stem cells.

3. The method of claim 2, further comprising aspirating autogenous bone marrow to obtain said autogenous bone marrow concentrate.

4. The method of claim 3, further comprising aspirating said autogenous bone marrow to obtain about 5 milliliters to about 55 milliliters of said autogenous bone marrow concentrate.

5. The method of claim 4, further comprising aspirating autogenous bone marrow of an ilium of a pelvis.

6. The method of claim 1, further comprising injecting said autogenous mesenchymal stem cells into a trabecular bone of said tibial metaphysis of said tibia.

7. The method of claim 6, further comprising injecting said autogenous mesenchymal stem cells into said trabecular bone of said tibial metaphysis of said tibia at a location of between about 1 centimeter to about 2 centimeters below the tibial plateau.

8. The method of claim 7, further comprising injecting said autogenous mesenchymal stem cells into a trabecular bone of said tibial metaphysis of said tibia at a depth of between about 1 centimeter to about 2 centimeters.

9. The method of claim 6, further comprising injecting said autogenous mesenchymal stem cells into a trabecular bone of said tibial metaphysis of said tibia at a depth of between about 1 centimeter to about 2 centimeters.

10. The method of claim 9, further comprising injecting said autogenous mesenchymal stem cells into said trabecular bone of said tibial metaphysis of said tibia at a location of between about 1 centimeter to about 2 centimeters below the tibial plateau.

11. The method of any one of claim 7 or 9, further comprising injecting an autogenous bone marrow concentrate containing said autogenous mesenchymal stem cells.

12. The method of claim 6, further comprising injecting autogenous bone marrow concentrate containing said autogenous mesenchymal stem cells into said trabecular bone of said tibial metaphysis of said tibia.

13. The method of claim 11, further comprising injecting between about 5 milliliters to about 10 milliliters of said autogenous bone marrow concentrate containing said autogenous mesenchymal stem cells into said trabecular bone of said tibial metaphysis of said tibia.

14. The method of claim 13, further comprising injecting between said about 5 milliliters to about 10 milliliters of said autogenous bone marrow concentrate containing said autogenous mesenchymal stem cells into said trabecular bone of said tibial metaphysis of said tibia at a rate of about 1 milliliter per about 5 seconds to about 15 seconds.

15. The method of claim 12, further comprising injecting said autogenous mesenchymal stem cells into said trabecular bone of said tibial metaphysis of said tibia at a location of between about 1 centimeter to about 2 centimeters below the tibial plateau.

16. The method of claim 15, further comprising injecting said autogenous mesenchymal stem cells into a trabecular bone of said tibial metaphysis of said tibia at a depth of between about 1 centimeter to about 2 centimeters.

17. The method of any one of claim 6 or 12, further comprising plugging said entry spot of injection into said tibia.

18. The method of claim 1, further comprising injecting said autogenous mesenchymal stem cells into a medial tibial compartment of said knee.

19. The method of claim 18, further comprising injecting autogenous bone marrow concentrate containing said autogenous mesenchymal stem cells into said tibial metaphysis of a tibia and said medial tibial compartment of said knee.

20. The method of claim 19, further comprising injecting about 5 milliliters and about 10 milliliters of said autogenous bone marrow concentrate containing said autogenous mesenchymal stem cells into each of said tibial metaphysis of a tibia and into said medial tibial compartment of said knee.

21. The method of claim 20, further comprising injecting between said about 5 milliliters to about 10 milliliters of said autogenous bone marrow concentrate containing said autogenous mesenchymal stem cells into said trabecular bone of said tibial metaphysis of said tibia at a rate of about 1 milliliter each about 5 seconds to about 15 seconds.

22. The method of claim 1, further comprising regenerating said tibial metaphysis toward a normal physiologic structure.

23. A method for treating inflammation in an osteoarthritic knee to regenerate the tibial metaphysis of the knee toward a normal physiologic structure, comprising:
   (a) obtaining autogenous mesenchymal stem cells;
   (b) injecting said autogenous mesenchymal stem cells into a tibial metaphysis of a tibia;
   (c) reducing the inflammation; and,
   (d) regenerating said tibial metaphysis toward a normal physiologic structure.

24. The method of claim 23, further comprising obtaining autogenous bone marrow concentrate containing said autogenous mesenchymal stem cells.

25. The method of claim 24, further comprising aspirating autogenous bone marrow to obtain said autogenous bone marrow concentrate.

26. The method of claim 25, further comprising aspirating said autogenous bone marrow to obtain about 5 milliliters to about 55 milliliters of said autogenous bone marrow concentrate.

27. The method of claim 26, further comprising aspirating autogenous bone marrow of an ilium of a pelvis.

28. The method of claim 23, further comprising injecting said autogenous mesenchymal stem cells into a trabecular bone of said tibial metaphysis of said tibia.

29. The method of claim 28, further comprising injecting said autogenous mesenchymal stem cells into said trabecular bone of said tibial metaphysis of said tibia at a location of between about 1 centimeter to about 2 centimeters below the tibial plateau.

30. The method of claim 29, further comprising injecting said autogenous mesenchymal stem cells into a trabecular bone of said tibial metaphysis of said tibia at a depth of between about 1 centimeter to about 2 centimeters.

31. The method of claim 28, further comprising injecting said autogenous mesenchymal stem cells into a trabecular bone of said tibial metaphysis of said tibia at a depth of between about 1 centimeter to about 2 centimeters.

32. The method of claim 31, further comprising injecting said autogenous mesenchymal stem cells into said trabecular bone of said tibial metaphysis of said tibia at a location of between about 1 centimeter to about 2 centimeters below the tibial plateau.

33. The method of any one of claim 29 or 31, further comprising injecting an autogenous bone marrow concentrate containing said autogenous mesenchymal stem cells.

34. The method of claim 28, further comprising injecting autogenous bone marrow concentrate containing said autogenous mesenchymal stem cells into said trabecular bone of said tibial metaphysis of said tibia.

35. The method of claim 34, further comprising injecting between about 5 milliliters to about 10 milliliters of said autogenous bone marrow concentrate containing said autogenous mesenchymal stem cells into said trabecular bone of said tibial metaphysis of said tibia.

36. The method of claim 35, further comprising injecting between said about 5 milliliters to about 10 milliliters of said autogenous bone marrow concentrate containing said autogenous mesenchymal stem cells into said trabecular bone of said tibial metaphysis of said tibia at a rate of about 1 milliliter per about 5 seconds to about 15 seconds.

37. The method of claim 36, further comprising injecting said autogenous mesenchymal stem cells into said trabecular bone of said tibial metaphysis of said tibia at a location of between about 1 centimeter to about 2 centimeters below the tibial plateau.

38. The method of claim 37, further comprising injecting said autogenous mesenchymal stem cells into a trabecular bone of said tibial metaphysis of said tibia at a depth of between about 1 centimeter to about 2 centimeters.

39. The method of any one of claim 28 or 34, further comprising plugging said entry spot of injection into said tibia.

40. The method of claim 23, further comprising injecting said autogenous mesenchymal stem cells into a medial tibial compartment of said knee.

41. The method of claim 40, further comprising injecting autogenous bone marrow concentrate containing said autogenous mesenchymal stem cells into said tibial metaphysis of a tibia and said medial tibial compartment of said knee.

42. The method of claim 41, further comprising injecting about 5 milliliters and about 10 milliliters of said autogenous bone marrow concentrate containing said autogenous mesenchymal stem cells into each of said tibial metaphysis of a tibia and into said a medial tibial compartment of said knee.

43. The method of claim 42, further comprising injecting between said about 5 milliliters to about 10 milliliters of said autogenous bone marrow concentrate containing said autogenous mesenchymal stem cells into said trabecular bone of said tibial metaphysis of said tibia at a rate of about 1 milliliter each about 5 seconds to about 15 seconds.

44. The method of claim 23, further comprising alleviating symptoms of said osteoarthritis of the knee.

\* \* \* \* \*